US010987239B2

(12) United States Patent
Longo et al.

(10) Patent No.: US 10,987,239 B2
(45) Date of Patent: *Apr. 27, 2021

(54) ROTARY HANDLE STENT DELIVERY SYSTEM AND METHOD

(71) Applicant: Vesper Medical, Inc., Wayne, PA (US)

(72) Inventors: Michael A. Longo, Glenmoore, PA (US); Timothy W. O'Neil, King of Prussia, PA (US); Christopher John Turek, West Chester, PA (US)

(73) Assignee: Vesper Medical, Inc., Wayne, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/599,444

(22) Filed: Oct. 11, 2019

(65) Prior Publication Data

US 2020/0038214 A1 Feb. 6, 2020

Related U.S. Application Data

(63) Continuation of application No. 15/993,291, filed on May 30, 2018, now Pat. No. 10,441,449.

(51) Int. Cl.
*A61F 2/966* (2013.01)
*A61F 2/95* (2013.01)
*A61M 25/01* (2006.01)

(52) U.S. Cl.
CPC ............ *A61F 2/966* (2013.01); *A61F 2/9517* (2020.05); *A61M 25/0113* (2013.01)

(58) Field of Classification Search
CPC .. A61F 2/95; A61F 2/962; A61F 2/966; A61F 2002/9517; A61F 2/2427;
(Continued)

(56) References Cited

U.S. PATENT DOCUMENTS 4,665,918 A 5/1987 Garza et al.
5,415,664 A 5/1995 Pinchuk
(Continued)

FOREIGN PATENT DOCUMENTS

DE 29717110 U1 11/1997
DE 19819634 11/1999
(Continued)

OTHER PUBLICATIONS

International Search Report and Written Opinion issued for Application No. PCT/US2019/034371, dated Aug. 19, 2019.
(Continued)

*Primary Examiner* — Diane D Yabut
*Assistant Examiner* — Christian D Knauss
(74) *Attorney, Agent, or Firm* — Meunier Carlin & Curfman LLC

(57) ABSTRACT

A delivery device according to principles described herein includes a catheter having three concentric shafts including an inner core, an outer sheath over the inner core and an outer support shaft at least partially extending over the inner core and the outer sheath. A timing belt having a plurality of belt teeth on a surface of the timing belt is coupled to an outer sheath over a medical device or stent on the inner core such that movement of the timing belt link causes movement of the outer sheath from its position over the medical device or stent. The delivery device is actuated by rotation of a thumbwheel a thumbwheel coupled to a barrel having a plurality of teeth such that rotation of the thumbwheel causes movement of the barrel such that the barrel teeth engage the belt teeth to cause movement of the timing belt causing movement of the outer sheath.

28 Claims, 9 Drawing Sheets

(58) Field of Classification Search
CPC ...... A61F 2/243; A61F 2/2436; A61F 2/2439; A61F 2002/2484; A61M 25/0113
See application file for complete search history.

(56) References Cited

U.S. PATENT DOCUMENTS

| | | | |
|---|---|---|---|
| 5,417,708 | A | 5/1995 | Hall et al. |
| 5,433,723 | A | 7/1995 | Lindenberg et al. |
| 5,443,477 | A | 8/1995 | Marin et al. |
| 5,458,615 | A | 10/1995 | Klemm et al. |
| 5,484,444 | A | 1/1996 | Braunschweiler et al. |
| 5,501,654 | A | 3/1996 | Failla et al. |
| 5,507,768 | A | 4/1996 | Lau et al. |
| 5,571,168 | A | 11/1996 | Toro |
| 5,695,499 | A | 12/1997 | Helgerson et al. |
| 5,725,534 | A | 3/1998 | Rasmussen et al. |
| 5,759,186 | A | 6/1998 | Bachmann et al. |
| 5,788,707 | A | 8/1998 | Del Toro et al. |
| 5,800,517 | A | 9/1998 | Anderson et al. |
| 5,860,998 | A | 1/1999 | Robinson et al. |
| 5,906,619 | A | 5/1999 | Olson et al. |
| 5,944,727 | A | 8/1999 | Ahari et al. |
| 6,019,778 | A | 2/2000 | Wilson et al. |
| 6,113,608 | A | 9/2000 | Monroe et al. |
| 6,117,140 | A | 9/2000 | Munsinger |
| 6,165,166 | A | 12/2000 | Samuelson et al. |
| 6,203,550 | B1 | 3/2001 | Olson |
| 6,241,758 | B1 | 6/2001 | Cox et al. |
| 6,299,635 | B1 | 10/2001 | Frantzen |
| 6,302,893 | B1 | 10/2001 | Limon et al. |
| 6,402,760 | B1 | 6/2002 | Fedida |
| 6,599,296 | B1 | 7/2003 | Gillick et al. |
| 6,613,075 | B1 | 9/2003 | Healy et al. |
| 6,620,550 | B2 | 9/2003 | Christian et al. |
| 6,669,716 | B1 | 12/2003 | Gilson et al. |
| 6,702,846 | B2 | 3/2004 | Mikus et al. |
| 6,755,854 | B2 | 6/2004 | Gillick et al. |
| 6,866,669 | B2 | 3/2005 | Buzzard et al. |
| 6,911,039 | B2 | 6/2005 | Shiu et al. |
| 6,939,352 | B2 | 9/2005 | Buzzard et al. |
| 7,033,368 | B2 | 4/2006 | Rourke |
| 7,052,511 | B2 | 5/2006 | Weldon et al. |
| 7,105,016 | B2 | 9/2006 | Shiu et al. |
| 7,182,779 | B2 | 2/2007 | Acosta et al. |
| 7,278,998 | B2 | 10/2007 | Gaschino et al. |
| 7,300,456 | B2 | 11/2007 | Andreas et al. |
| 7,309,350 | B2 | 12/2007 | Landreville et al. |
| 7,326,236 | B2 | 2/2008 | Andreas et al. |
| 7,381,216 | B2 | 6/2008 | Buzzard et al. |
| D576,725 | S | 9/2008 | Shumer et al. |
| 7,419,501 | B2 | 9/2008 | Chiu et al. |
| D578,216 | S | 10/2008 | Dorn et al. |
| D578,643 | S | 10/2008 | Shumer et al. |
| D578,644 | S | 10/2008 | Shumer et al. |
| D578,645 | S | 10/2008 | Shumer et al. |
| 7,476,244 | B2 | 1/2009 | Buzzard et al. |
| 7,550,001 | B2 | 6/2009 | Dorn et al. |
| 7,553,322 | B2 | 6/2009 | Dorn et al. |
| 7,553,324 | B2 | 6/2009 | Andreas et al. |
| 7,660,621 | B2 | 2/2010 | Skakoon et al. |
| 7,674,282 | B2 | 3/2010 | Wu et al. |
| 7,758,625 | B2 | 7/2010 | Wu et al. |
| 7,780,716 | B2 | 8/2010 | Pappas et al. |
| 7,794,489 | B2 | 9/2010 | Shumer et al. |
| 7,799,065 | B2 | 9/2010 | Pappas et al. |
| 7,815,669 | B2 | 10/2010 | Matsuoka et al. |
| 7,819,882 | B2 | 10/2010 | Rourke |
| 7,892,274 | B2 | 2/2011 | Will et al. |
| 7,935,141 | B2 | 5/2011 | Randall et al. |
| 7,963,987 | B2 | 6/2011 | Melsheimer et al. |
| 7,967,829 | B2 | 6/2011 | Gunderson et al. |
| 7,976,574 | B2 | 7/2011 | Papp |
| 7,993,384 | B2 | 8/2011 | Wu et al. |
| 8,016,870 | B2 | 9/2011 | Chew |
| 8,062,344 | B2 | 11/2011 | Dorn et al. |
| 8,075,607 | B2 | 12/2011 | Melsheimer |
| 8,092,468 | B2 | 1/2012 | Hansen |
| 8,157,851 | B2 | 4/2012 | Andreas |
| 8,177,831 | B2 | 5/2012 | Andreas |
| 8,216,296 | B2 | 7/2012 | Wu et al. |
| 8,382,813 | B2 | 2/2013 | Shumer |
| D678,512 | S | 3/2013 | Bow |
| 8,416,636 | B2 | 4/2013 | Carman et al. |
| 8,419,784 | B2 | 4/2013 | Matsuoka et al. |
| 8,486,128 | B2 | 7/2013 | Jen et al. |
| 8,500,789 | B2 | 8/2013 | Wueebbeling et al. |
| 8,500,792 | B2 | 8/2013 | Berra |
| 8,585,747 | B2 | 11/2013 | Andreas et al. |
| 8,778,006 | B2 | 7/2014 | Fargahi et al. |
| 8,784,468 | B2 | 7/2014 | Gerdts et al. |
| 8,808,346 | B2 | 8/2014 | Jimenez, Jr. et al. |
| 8,828,072 | B2 | 9/2014 | Hoffman et al. |
| 8,852,266 | B2 | 10/2014 | Brooks et al. |
| 8,864,811 | B2 | 10/2014 | Kao |
| 8,888,834 | B2 | 11/2014 | Hansen et al. |
| 8,911,487 | B2 | 12/2014 | Bennett et al. |
| 8,951,297 | B2 | 2/2015 | Kawakita |
| 8,956,398 | B2 | 2/2015 | George et al. |
| 8,986,362 | B2 | 3/2015 | Snow et al. |
| 8,986,363 | B2 | 3/2015 | McHugo et al. |
| 9,039,750 | B2 | 5/2015 | Ryan et al. |
| 9,138,315 | B2 | 9/2015 | Straubinger et al. |
| 9,149,379 | B2 | 10/2015 | Keady et al. |
| 9,301,864 | B2 | 4/2016 | Kao |
| 9,314,360 | B2 | 4/2016 | Kao |
| 9,320,591 | B2 | 4/2016 | Bolduc |
| 9,408,736 | B2 | 8/2016 | Loewen |
| 9,421,115 | B2 | 8/2016 | Wübbeling et al. |
| 9,445,928 | B2 | 9/2016 | Argentine |
| 9,539,130 | B2 | 1/2017 | Farag et al. |
| D779,053 | S | 2/2017 | Kobida et al. |
| 9,566,179 | B2 | 2/2017 | Andreas et al. |
| 9,622,894 | B2 | 4/2017 | McGee |
| D786,429 | S | 5/2017 | Cummins et al. |
| 9,662,236 | B2 | 5/2017 | Masubuchi |
| 9,675,486 | B2 | 6/2017 | Jimenez, Jr. et al. |
| D795,425 | S | 8/2017 | Cummins |
| 9,744,021 | B2 | 8/2017 | Bolduc |
| 9,765,858 | B2 | 9/2017 | Kelly |
| 9,849,016 | B2 | 12/2017 | Beard et al. |
| 9,872,785 | B2 | 1/2018 | Dorn et al. |
| 9,878,127 | B2 | 1/2018 | Damm et al. |
| 9,901,468 | B2 | 2/2018 | Harada |
| 9,913,741 | B2 | 3/2018 | Melsheimer et al. |
| 9,918,835 | B2 | 3/2018 | Guyenot et al. |
| 9,974,677 | B2 | 5/2018 | Costello |
| 9,974,678 | B2 | 5/2018 | Cummins |
| 10,016,292 | B2 | 7/2018 | Senness et al. |
| 2001/0004696 | A1 | 6/2001 | Roberts et al. |
| 2001/0012944 | A1 | 8/2001 | Bicek et al. |
| 2001/0027323 | A1 | 10/2001 | Sullivan et al. |
| 2001/0047150 | A1 | 11/2001 | Chobotov |
| 2002/0007138 | A1 | 1/2002 | Wilk et al. |
| 2002/0007206 | A1 | 1/2002 | Bui et al. |
| 2002/0029075 | A1 | 3/2002 | Leonhardt |
| 2002/0065545 | A1 | 5/2002 | Leonhardt |
| 2002/0128707 | A1 | 9/2002 | Kavteladze |
| 2002/0151953 | A1 | 10/2002 | Chobotov et al. |
| 2003/0009174 | A1 | 1/2003 | Smith |
| 2003/0036791 | A1 | 2/2003 | Philipp et al. |
| 2003/0040789 | A1 | 2/2003 | Colgan et al. |
| 2003/0045893 | A1 | 3/2003 | Ginn |
| 2003/0050686 | A1 | 3/2003 | Raeder-Devens et al. |
| 2003/0074045 | A1 | 4/2003 | Buzzard et al. |
| 2003/0120331 | A1 | 6/2003 | Chobotov et al. |
| 2003/0149469 | A1 | 8/2003 | Wolinsky et al. |
| 2003/0149476 | A1 | 8/2003 | Damm et al. |
| 2003/0149478 | A1 | 8/2003 | Figulla et al. |
| 2003/0153941 | A1 | 8/2003 | Rourke |
| 2003/0167087 | A1 | 9/2003 | Piplani et al. |
| 2003/0191516 | A1 | 10/2003 | Weldon et al. |
| 2004/0006380 | A1 | 1/2004 | Buck et al. |
| 2004/0093056 | A1 | 5/2004 | Johnson et al. |
| 2004/0106977 | A1 | 6/2004 | Sullivan et al. |

(56) References Cited

U.S. PATENT DOCUMENTS

| | | |
|---|---|---|
| 2004/0153137 A1 | 8/2004 | Gaschino et al. |
| 2004/0167619 A1 | 8/2004 | Case et al. |
| 2004/0181239 A1 | 9/2004 | Dorn et al. |
| 2004/0193243 A1 | 9/2004 | Mangiardi et al. |
| 2004/0199240 A1 | 10/2004 | Dorn |
| 2004/0210188 A1 | 10/2004 | Glines et al. |
| 2005/0027345 A1 | 2/2005 | Horan et al. |
| 2005/0033403 A1 | 2/2005 | Ward et al. |
| 2005/0038493 A1 | 2/2005 | Feeser |
| 2005/0060016 A1 | 3/2005 | Wu et al. |
| 2005/0080476 A1 | 4/2005 | Gunderson et al. |
| 2005/0090887 A1 | 4/2005 | Pryor |
| 2005/0090890 A1 | 4/2005 | Wu |
| 2005/0137686 A1 | 6/2005 | Salahieh et al. |
| 2005/0149159 A1 | 7/2005 | Andreas et al. |
| 2005/0149160 A1 | 7/2005 | McFerran |
| 2005/0182475 A1 | 8/2005 | Jen et al. |
| 2005/0232961 A1 | 10/2005 | Lowe et al. |
| 2005/0256562 A1* | 11/2005 | Clerc ............... A61F 2/95 623/1.11 |
| 2005/0273151 A1* | 12/2005 | Fulkerson ............... A61F 2/966 623/1.11 |
| 2005/0288763 A1 | 12/2005 | Andreas et al. |
| 2006/0009833 A1 | 1/2006 | Chobotov et al. |
| 2006/0020321 A1 | 1/2006 | Parker |
| 2006/0142833 A1 | 6/2006 | Von Oepen et al. |
| 2006/0212105 A1 | 9/2006 | Dorn et al. |
| 2006/0229711 A1 | 10/2006 | Yan et al. |
| 2006/0247661 A1 | 11/2006 | Richards et al. |
| 2006/0259124 A1 | 11/2006 | Matsuoka et al. |
| 2006/0286145 A1 | 12/2006 | Horan et al. |
| 2007/0055340 A1 | 3/2007 | Pryor |
| 2007/0060999 A1 | 3/2007 | Randall et al. |
| 2007/0088421 A1 | 4/2007 | Loewen |
| 2007/0100440 A1 | 5/2007 | Figulla et al. |
| 2007/0112355 A1 | 5/2007 | Salahieh et al. |
| 2007/0118079 A1 | 5/2007 | Moberg et al. |
| 2007/0142906 A1 | 6/2007 | Figulla et al. |
| 2007/0156224 A1 | 7/2007 | Cioanta et al. |
| 2007/0162127 A1 | 7/2007 | Peterman et al. |
| 2007/0168014 A1 | 7/2007 | Jimenez et al. |
| 2007/0185558 A1 | 8/2007 | Hartley |
| 2007/0191925 A1 | 8/2007 | Dorn |
| 2007/0213813 A1 | 9/2007 | Von Segesser et al. |
| 2007/0219617 A1 | 9/2007 | Saint |
| 2008/0082154 A1 | 4/2008 | Tseng et al. |
| 2008/0154293 A1 | 6/2008 | Taylor |
| 2008/0188920 A1 | 8/2008 | Moberg et al. |
| 2008/0255660 A1 | 10/2008 | Guyenot et al. |
| 2009/0005760 A1 | 1/2009 | Cartledge et al. |
| 2009/0024133 A1 | 1/2009 | Keady et al. |
| 2009/0024137 A1 | 1/2009 | Chuter et al. |
| 2009/0171428 A1 | 7/2009 | Hansen |
| 2009/0177264 A1 | 7/2009 | Ravenscroft |
| 2009/0210046 A1 | 8/2009 | Shumer et al. |
| 2009/0216310 A1 | 8/2009 | Straubinger et al. |
| 2009/0234443 A1 | 9/2009 | Ottma et al. |
| 2009/0312831 A1 | 12/2009 | Dorn |
| 2010/0004606 A1* | 1/2010 | Hansen ............... A61F 2/95 604/264 |
| 2010/0004730 A1 | 1/2010 | Benjamin et al. |
| 2010/0036472 A1 | 2/2010 | Papp |
| 2010/0076541 A1 | 3/2010 | Kumoyama |
| 2010/0125280 A1 | 5/2010 | Molloy |
| 2010/0137967 A1 | 6/2010 | Atlani et al. |
| 2010/0168756 A1 | 7/2010 | Dorn et al. |
| 2010/0168834 A1 | 7/2010 | Ryan et al. |
| 2010/0174290 A1 | 7/2010 | Wueebbeling et al. |
| 2010/0292779 A1 | 11/2010 | Straubinger et al. |
| 2011/0056064 A1 | 3/2011 | Malewicz et al. |
| 2011/0190862 A1 | 8/2011 | Bashiri et al. |
| 2011/0190865 A1 | 8/2011 | McHugo et al. |
| 2011/0288626 A1 | 11/2011 | Straubinger et al. |
| 2011/0295363 A1 | 12/2011 | Girard et al. |
| 2011/0319989 A1 | 12/2011 | Lane et al. |
| 2012/0022631 A1 | 1/2012 | Costello |
| 2012/0022632 A1 | 1/2012 | Hoffman et al. |
| 2012/0022635 A1 | 1/2012 | Yamashita |
| 2012/0029607 A1 | 2/2012 | McHugo et al. |
| 2012/0041450 A1 | 2/2012 | Awtar et al. |
| 2012/0053671 A1 | 3/2012 | McHugo et al. |
| 2012/0116493 A1 | 5/2012 | Harada |
| 2012/0123516 A1 | 5/2012 | Gerdts et al. |
| 2012/0158117 A1 | 6/2012 | Ryan |
| 2012/0209175 A1 | 8/2012 | Moelgaard-Nielsen |
| 2012/0209366 A1 | 8/2012 | Sudo et al. |
| 2012/0226341 A1 | 9/2012 | Schreck et al. |
| 2012/0265288 A1 | 10/2012 | Jones et al. |
| 2012/0310321 A1 | 12/2012 | Beach et al. |
| 2012/0330401 A1 | 12/2012 | Sugimoto et al. |
| 2013/0013057 A1 | 1/2013 | Salahieh et al. |
| 2013/0018451 A1* | 1/2013 | Grabowski ............... A61F 2/966 623/1.12 |
| 2013/0079864 A1 | 3/2013 | Boden et al. |
| 2013/0085562 A1 | 4/2013 | Rincon et al. |
| 2013/0103130 A1 | 4/2013 | Lubinski et al. |
| 2013/0184805 A1 | 7/2013 | Sawada |
| 2013/0211493 A1 | 8/2013 | Wubbeling et al. |
| 2013/0268048 A1 | 10/2013 | Watson et al. |
| 2013/0268049 A1 | 10/2013 | Munsinger et al. |
| 2013/0304189 A1 | 11/2013 | Shimoyama |
| 2013/0338752 A1 | 12/2013 | Geusen et al. |
| 2014/0025155 A1 | 1/2014 | Masubuchi |
| 2014/0081252 A1 | 3/2014 | Bowe et al. |
| 2014/0107673 A1 | 4/2014 | Snyder et al. |
| 2014/0121674 A1 | 5/2014 | Staunton |
| 2014/0121755 A1 | 5/2014 | Farag et al. |
| 2014/0180380 A1 | 6/2014 | Kelly |
| 2014/0257454 A1 | 9/2014 | McGee |
| 2014/0257459 A1 | 9/2014 | Masakazu |
| 2014/0276682 A1 | 9/2014 | Hendrick et al. |
| 2014/0277037 A1 | 9/2014 | Grace et al. |
| 2014/0277321 A1 | 9/2014 | Grace |
| 2014/0277349 A1 | 9/2014 | Vad |
| 2014/0343601 A1 | 11/2014 | Abbott et al. |
| 2014/0343660 A1 | 11/2014 | Shimoyama |
| 2015/0025615 A1 | 1/2015 | Brooks et al. |
| 2015/0051688 A1 | 2/2015 | Cummins |
| 2015/0057739 A1 | 2/2015 | Costello |
| 2015/0057741 A1 | 2/2015 | Ryan |
| 2015/0065280 A1 | 3/2015 | Kelly |
| 2015/0094794 A1 | 4/2015 | Cummins et al. |
| 2015/0105796 A1 | 4/2015 | Grace |
| 2015/0119800 A1 | 4/2015 | Neoh et al. |
| 2015/0127092 A1 | 5/2015 | Straubinger et al. |
| 2015/0148894 A1 | 5/2015 | Damm et al. |
| 2015/0230954 A1 | 8/2015 | McHugo |
| 2015/0238315 A1 | 8/2015 | Rabito et al. |
| 2015/0238730 A1 | 8/2015 | Corman et al. |
| 2015/0250631 A1 | 9/2015 | Cummins et al. |
| 2015/0265445 A1 | 9/2015 | Weber et al. |
| 2015/0282881 A1 | 10/2015 | Beard et al. |
| 2015/0297378 A1 | 10/2015 | Senness et al. |
| 2015/0335333 A1 | 11/2015 | Jones et al. |
| 2015/0343121 A1 | 12/2015 | Kobida et al. |
| 2016/0074184 A1 | 3/2016 | Cummins et al. |
| 2016/0074189 A1 | 3/2016 | Cummins |
| 2016/0123441 A1 | 5/2016 | Gillick et al. |
| 2016/0135972 A1 | 5/2016 | Vad et al. |
| 2016/0135975 A1 | 5/2016 | Shimoyama |
| 2016/0158010 A1 | 6/2016 | Lim et al. |
| 2016/0158049 A1 | 6/2016 | Dooley |
| 2016/0213465 A1 | 7/2016 | Girard et al. |
| 2016/0235568 A1 | 8/2016 | Green |
| 2016/0262883 A1 | 9/2016 | Sandstrom |
| 2016/0303734 A1 | 10/2016 | Bowles et al. |
| 2017/0035590 A1 | 2/2017 | Watson et al. |
| 2017/0348100 A1 | 2/2017 | Lane et al. |
| 2017/0056156 A1 | 3/2017 | Ryan |
| 2017/0095236 A1 | 4/2017 | Sharma et al. |
| 2017/0095330 A1 | 4/2017 | Malewicz et al. |
| 2017/0095922 A1 | 4/2017 | Licht et al. |
| 2017/0172773 A1 | 6/2017 | Gong et al. |
| 2017/0216063 A1 | 8/2017 | Bessho |

(56) References Cited

U.S. PATENT DOCUMENTS

| | | | |
|---|---|---|---|
| 2017/0348087 | A1 | 12/2017 | Chobotov et al. |
| 2018/0021132 | A1 | 1/2018 | Ottma et al. |
| 2018/0080533 | A1 | 3/2018 | Awtar |
| 2018/0098849 | A1 | 4/2018 | Yellin et al. |
| 2018/0133006 | A1 | 5/2018 | Jones et al. |
| 2018/0133007 | A1 | 5/2018 | Prabhu |
| 2018/0147076 | A1 | 5/2018 | Cummins et al. |
| 2018/0153693 | A1 | 6/2018 | Copeland et al. |
| 2018/0153694 | A1 | 6/2018 | Wilson et al. |
| 2018/0206976 | A1 | 7/2018 | Cartledge et al. |

FOREIGN PATENT DOCUMENTS

| | | |
|---|---|---|
| DE | 102013015896 | 3/2015 |
| EP | 3354237 | 8/2018 |
| JP | 2008132027 | 6/2008 |
| JP | 2012187177 | 10/2012 |
| KR | 101685325 | 12/2016 |
| WO | 2008034793 | 3/2008 |
| WO | 2008124844 | 10/2008 |
| WO | 2017052414 | 3/2017 |
| WO | 2018107123 | 6/2018 |

OTHER PUBLICATIONS

International Search Report and Written Opinion issued for Application No. PCT/US2019/034376, dated Oct. 30, 2019.

Office Action issued for U.S. Appl. No. 16/134,287, dated Apr. 5, 2019.

Notice of Allowance issued for U.S. Appl. No. 16/134,287, dated Jul. 26, 2019.

Notice of Allowance issued for U.S. Appl. No. 16/134,287, dated Sep. 10, 2019.

Office Action issued for U.S. Appl. No. 15/993,291, dated Jul. 27, 2018.

Office Action issued for U.S. Appl. No. 15/993,291, dated Feb. 25, 2019.

Notice of Allowance issued for U.S. Appl. No. 15/993,291, dated May 23, 2019.

Notice of Allowance issued for U.S. Appl. No. 15/993,291, dated Sep. 12, 2019.

Office Action issued for U.S. Appl. No. 16/599,461, dated Nov. 29, 2019.

* cited by examiner

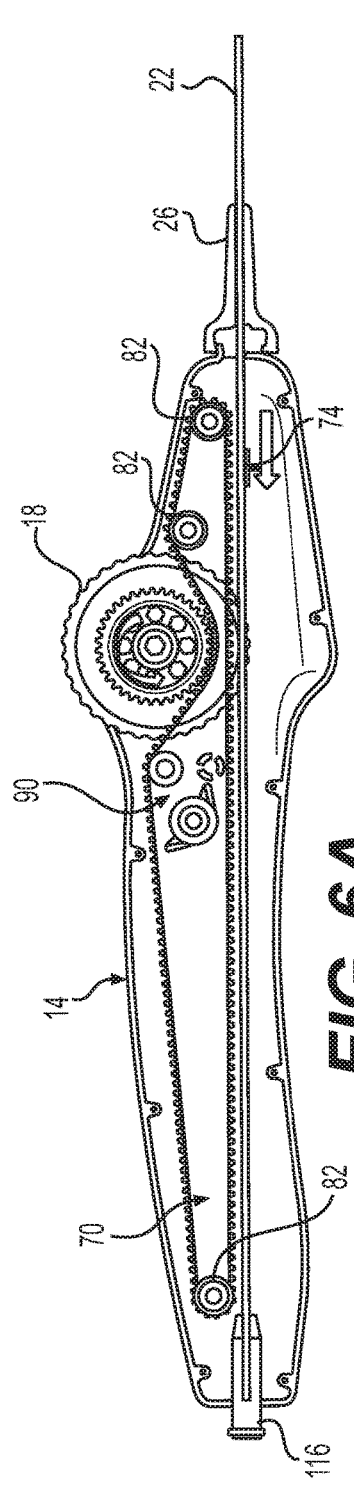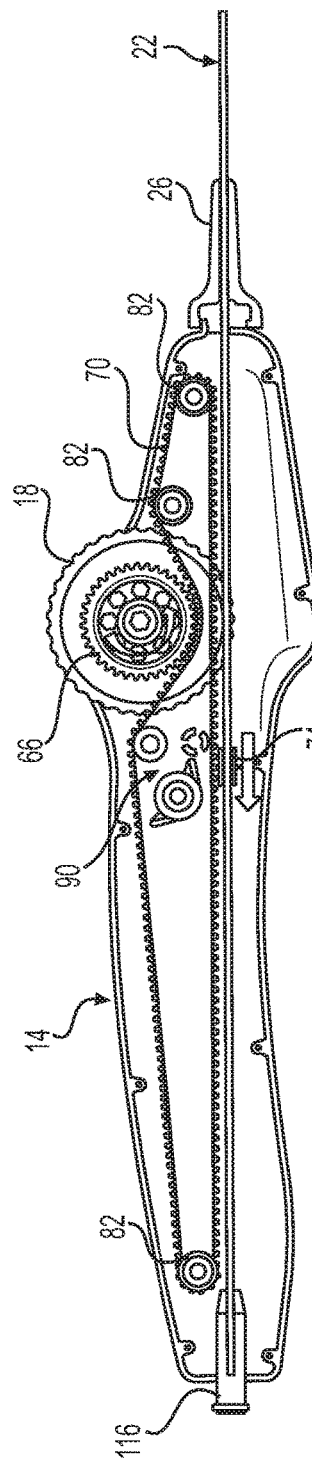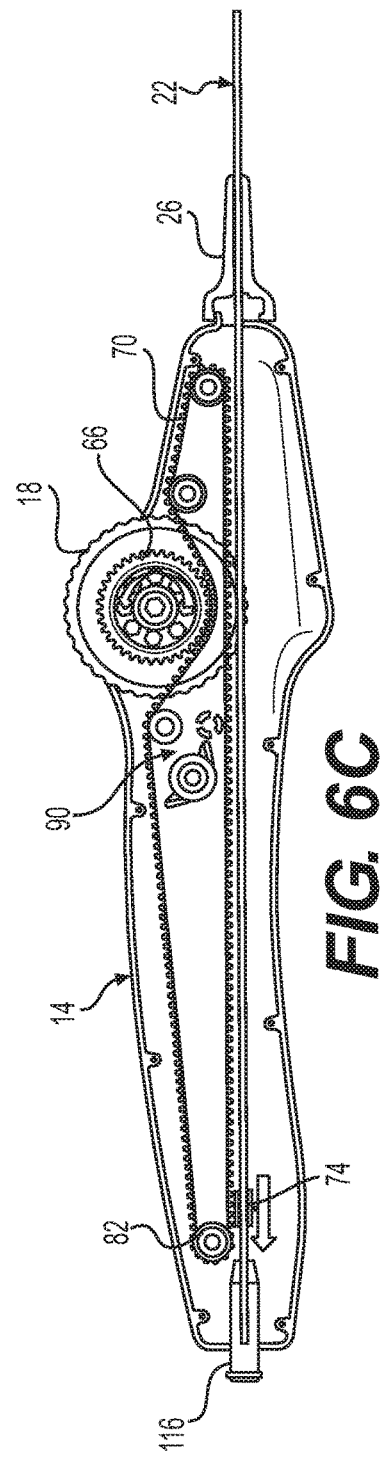

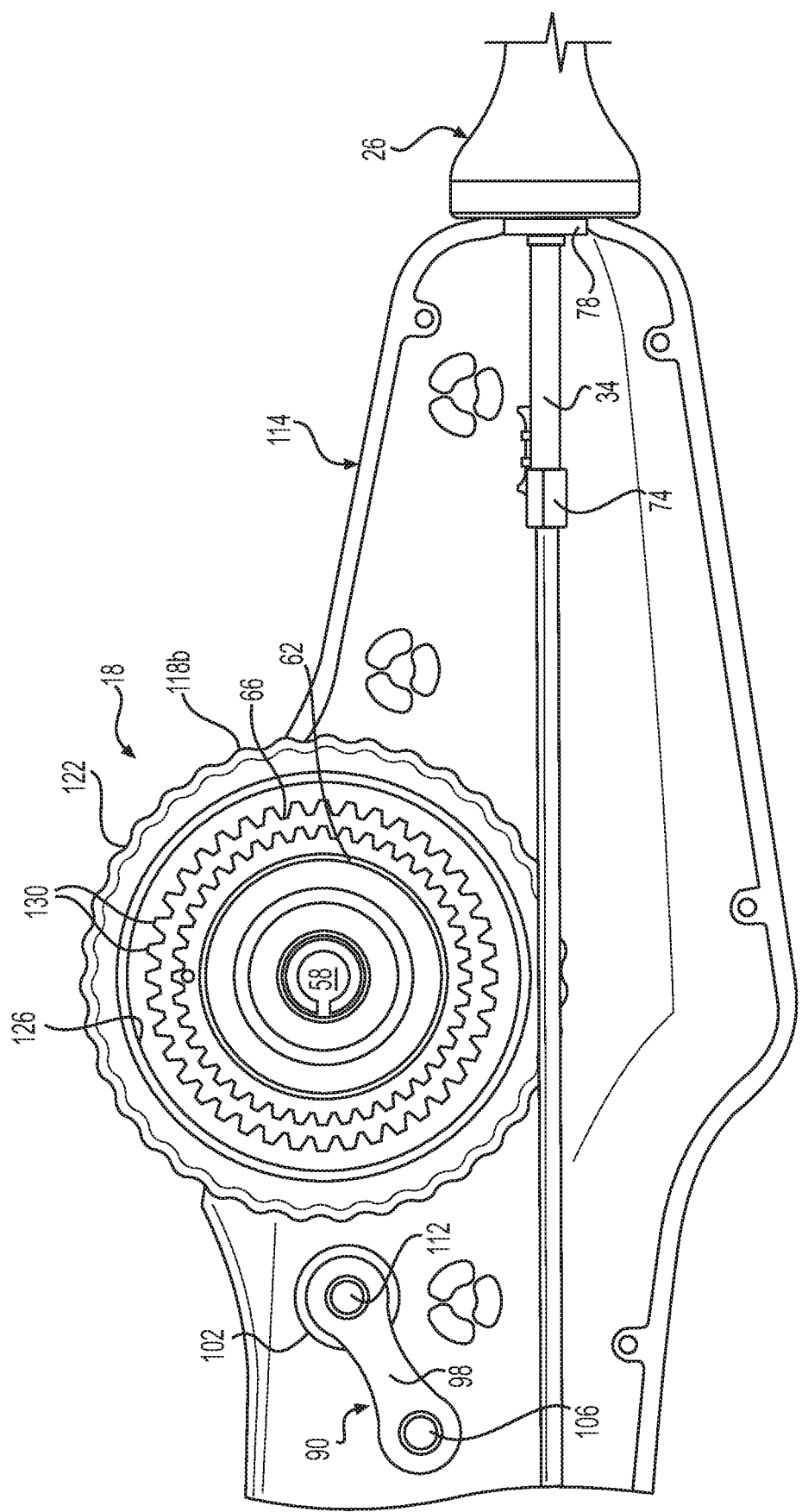

ROTARY HANDLE STENT DELIVERY SYSTEM AND METHOD

This application is a continuation application of U.S. patent application Ser. No. 15/993,291, filed May 30, 2018, the disclosure of which is incorporated herein by reference in its entirety.

BACKGROUND OF THE INVENTION

Field of the Invention

Embodiments of the present invention relate to a stent delivery device, specifically a single-handed thumbwheel driven delivery handle.

Background

There are a number of medical conditions and procedures in which a device such as a stent is placed in the body to create or maintain a passage. There are a wide variety of stents used for different purposes, from expandable coronary, vascular and biliary stents, to plastic stents used to allow the flow of urine between kidney and bladder.

Self-expanding stents, as well as balloon expandable stents, may also be used to treat various issues with the vascular system, including, but not limited to May-Thurner Syndrome and Deep Vein Thrombosis.

Stents are usually delivered in a compressed condition to the target site and then, deployed at that location into an expanded condition to support the vessel and help maintain it in an open position. The delivery system used to implant or deploy at the stent target site in the diseased vessel using a delivery system.

Stents are commonly delivered using a catheter delivery system. A common type of delivery system for delivering a self-expanding stent is called a pull back delivery system. This type of delivery system utilizes two catheters or shafts which are concentrically arranged, one around another. The stent is carried axially around the distal end of the inner catheter or shaft. The stent is carried to the delivery site on the distal end of the delivery device, held in its compressed delivery position by the outer shaft or catheter. Once at the desired placement site, the outer shaft is pulled back, releasing the stent to self-expand.

BRIEF SUMMARY OF THE INVENTION

Accordingly, the present invention is directed to a rotary handle stent delivery system and method that obviates one or more of the problems due to limitations and disadvantages of the related art.

In accordance with the purpose(s) of this invention, as embodied and broadly described herein, this invention, in one aspect, relates to a delivery device according to principles described herein including a catheter having three concentric shafts including an inner core, an outer sheath over the inner core and an outer support shaft; a timing belt having a plurality of belt teeth on a surface of the timing belt; a timing belt link coupled to the outer sheath such that movement of the timing belt link causes movement of the outer sheath; a barrel having barrel teeth corresponding to belt teeth; and a thumbwheel coupled to the barrel such that rotation of the thumbwheel causes movement of the barrel such that the barrel teeth engage the belt teeth to cause movement of the timing belt causing movement of the outer sheath.

In another aspect, a system for delivery of an intraluminal stent according to principles described herein includes a delivery device with a catheter having three concentric shafts including an inner core having the intraluminal stent thereon; an outer sheath over the stent in an unexpanded state on the inner core therein, the outer sheath holding the stent in an unexpanded state, the outer sheath translatable coaxially over the inner core and the intraluminal stent; and an outer support shaft at least partially extending over the inner core and the outer sheath; a timing belt having a plurality of belt teeth on a surface of the timing belt; a timing belt link coupled to the outer sheath such that movement of the timing belt link causes movement of the outer sheath to expose the intraluminal stent; a barrel having barrel teeth corresponding to belt teeth; and a thumbwheel coupled to the barrel such that rotation of the thumbwheel causes movement of the barrel such that the barrel teeth engage the belt teeth to cause movement of the timing belt causing movement of the outer sheath.

In yet another aspect, a method of delivering an medical device to a body according to principles described herein uses a delivery device with a catheter having three concentric shafts including an inner core, an outer sheath over the inner core and an outer support shaft; a timing belt having a plurality of belt teeth on a surface of the timing belt; a timing belt link coupled to the outer sheath such that movement of the timing belt link causes movement of the outer sheath; a barrel having barrel teeth corresponding to belt teeth; a thumbwheel coupled to the barrel such that rotation of the thumbwheel causes movement of the barrel such that the barrel teeth engage the belt teeth to cause movement of the timing belt causing movement of the outer sheath; and a medical device over an outer diameter of the inner core; the method includes rotating the thumbwheel in a predetermined direction to cause the timing belt to move in direction associated with the predetermined direction of thumbwheel rotation to cause the timing belt link to move the outer sheath in a desired direction; and deploying the medical device from a distal end of the inner core to the body as the outer sheath moves in the desired direction.

Additional advantages will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

Further embodiments, features, and advantages of the rotary handle stent delivery system and method, as well as the structure and operation of the various embodiments of the rotary handle stent delivery system and method, are described in detail below with reference to the accompanying drawings.

It is to be understood that both the foregoing general description and the following detailed description are exemplary and explanatory only and are not restrictive of the invention as claimed.

BRIEF DESCRIPTION OF THE DRAWINGS

The accompanying figures, which are incorporated herein and form part of the specification, illustrate a rotary handle stent delivery system and method. Together with the description, the figures further serve to explain the principles of the rotary handle stent delivery system and method described herein and thereby enable a person skilled in the pertinent art to make and use the rotary handle stent delivery system and method.

FIGS. 6(a)-(c) are cross-sectional views of the delivery device according to principles described herein and illustrate motion of the timing belt link and outer sheath upon movement of the thumbwheel.

FIG. 9 is a cross-sectional line drawing showing detail of an exemplary embodiment of the thumbwheel assembly.

DETAILED DESCRIPTION

Reference will now be made in detail to embodiments of the rotary handle stent delivery system and method with reference to the accompanying figures. Various embodiments disclosed herein illustrate a device and associated method for delivering expandable stents or other medical devices to implant or deploy a stent or other medical device to a target site in the diseased vessel.

Figure 1A:
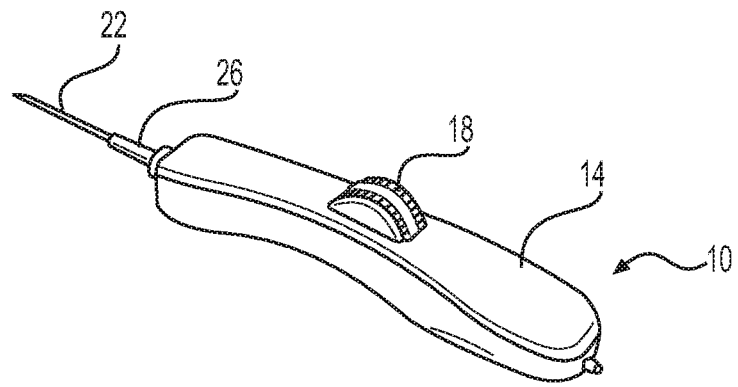
FIGS. 1(a)-(c) show various embodiments of a stent delivery handle according to principles described herein.
Figure 1B:
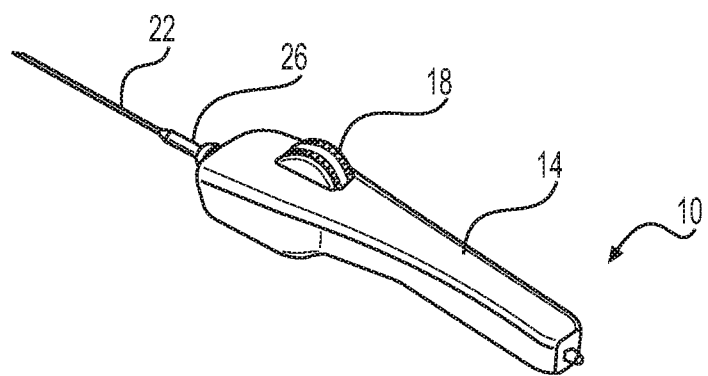
Figure 1C:
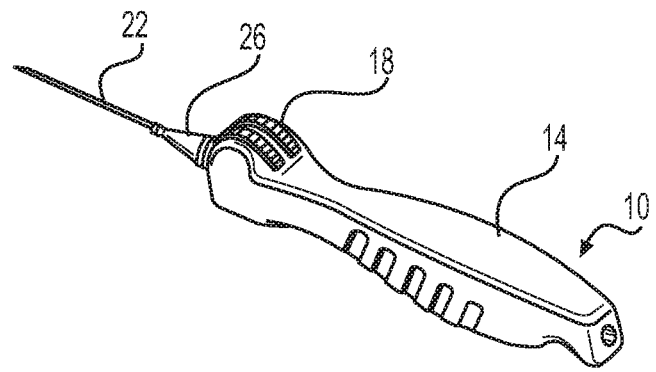

FIGS. 1(a)-(c) show various embodiments of a stent delivery handle according to principles described herein. As illustrated, the handle 10 includes a housing 14 and a thumbwheel/thumbwheel assembly 18, with a triaxial catheter 22 extending therefrom. The catheter may extend through strain relief 26 from the housing 10. The strain relief 26 can take any form, such as being made of polyolefin or other similar flexible material.

Figure 2:
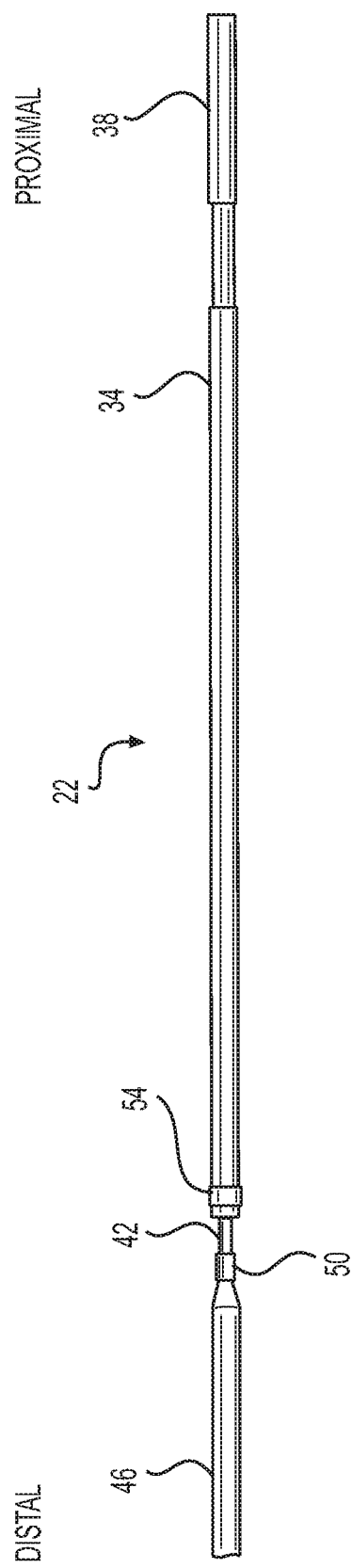
FIG. 2 illustrates an exemplary catheter configuration according to principles described herein.

Referring to FIG. 2, the catheter 22 includes three concentric or "coaxial" tubes/shafts (a triaxial design): inner core 42, outer sheath 34 and an outer support shaft 38. The outer sheath 34 may be tapered or stepped, as illustrated in FIG. 2, or may not be tapered, depending on the application. The outer support shaft 38 may be a PEEK (polyaryletheretherketone) tubing extrusion or other similar structure. The outer support shaft 38 can be manufactured from any semi-rigid material. PEEK exhibits good mechanical properties to provide support for the smaller diameter of the outer sheath and is flexible. PEEK is also an off-the-shelf component. A material other than PEEK may be used to form the outer support sheath, and the invention described herein is not limited to PEEK for use in the outer support shaft 38. Functionally, the outer support shaft 38 and inner core are fixed in position at the proximal end of the delivery system and the outer sheath translates coaxially over the inner core and inside the outer support shaft 38. A medical device such as a self-expanding stent (not shown) is held in a reduced delivery configuration for insertion and transport through a body lumen to a predetermined site for deployment. The stent (not shown) is carried axially around the inner core 42 and is held in its reduced delivery configuration by the outer sheath 34. The inner core 42 may be a braid reinforced tube that extends from the distal end to the proximal end of the device. In some embodiments, the inner core 42 may extend from the very distal end to the very proximal end (e.g. all the way from end to end). The inner diameter of the tube of the inner core 42 is sized for tracking over a guidewire and the outer diameter of the tube of the inner core 42 at the distal end is where the stent (not show) will be crimped between to inner core band markers (50). The outer support shaft 38 is used to stiffen the delivery device so that the arc of the inner core 42 will not change outside of the body when the outer sheath 34 is pulled back to release the stent (not shown) to self-expand. The outer support shaft 38 is connected to the handle 10 at the proximal end of the device, which stiffens the delivery system and reduces friction at the treatment insertion site so that the inner core 42 will not be urged forward as the middle shaft/outer sheath 34 is pulled backward. As illustrated in FIG. 2, the catheter 22 may include a distal tip 46. The inner core 42 may further include at least one inner core marker band 50 such that self-expanding stent is crimped and loaded at the distal end of the catheter and located over the inner core between two inner core marker bands 50 (only one is shown in FIG. 2) to prevent axial movement of the stent. The crimped and loaded self-expanding stent is circumferentially constrained by the outer sheath 34. The outer sheath 34 may also include an outer sheath marker band 54.

The triaxial design allows for more optimal delivery system stability and accurate placement during stent deployment as compared to a traditional 2-coaxial delivery system. The system in introduced into the body at an access location thorough an introducer sheath with hemostasis valve. Where the stent delivery system enters the introducer sheath into the body friction is generated at the hemostasis valve. Therefore, during deployment of a traditional 2-axis system as the outer sheath is being retracted, it wants to move relative to the introducer sheath due to friction, resulting in the inner core pushing out the stent versus retracting the outer sheath. The operator needs to compensate for this and move the entire delivery catheter while deploying the stent to maintain consistent placement during deployment. With long high radial force stents (such as venous stents) this can result in distal/proximal movement (accordion effect) of the entire delivery system during deployment of the stent and can result in inaccurate deployment or malposition of the stent. The triaxial design mitigates this effect as the outer support shaft 38 is inserted through the introducer sheath and therefore the friction between the outer sheath translation and introducer sheath hemostasis valve is eliminated.

Figure 3:
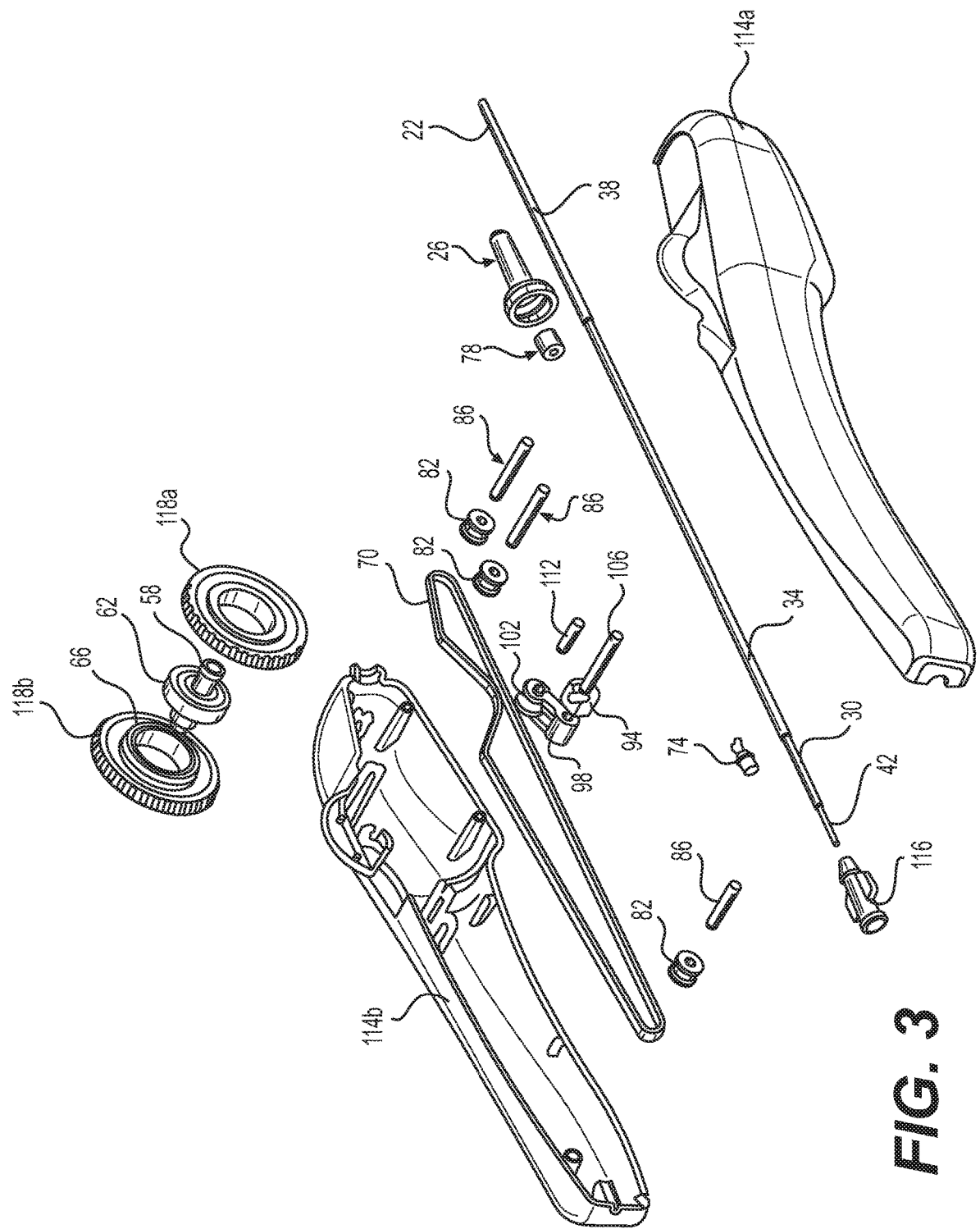
FIG. 3 illustrates is an exploded view of features of a delivery handle according to principles described herein.

FIG. 3 illustrates an exploded view of features of a delivery handle according to principles described herein. The exemplary embodiment illustrated in FIG. 3 includes a two-part housing 114a and 114b, where the respective two parts 114a and 114b may be snap fit together for assembly. The thumbwheel 18 may comprise two wheels 118a and 118b, an axle 58, and a bearing 62. The wheels 118a and 118b may include teeth on an inner barrel 66 thereof. Although only one inner barrel is shown in FIG. 3 on wheel 118b, wheel 118a may also include an inner barrel with teeth. The teeth on the inner barrel 66 are sized to correspond with teeth on a timing belt 70. A timing belt link 74 connects the outer sheath 34 to the timing belt 70. The housing may include a bushing 78, which may be a separate component or may be integral to the housing 14. The bushing may be formed of PEEK or other suitable material. The exemplary handle of FIG. 3 further includes at least one idler pulley 82 for tensioning and guiding the timing belt. Also shown in FIG. 3 idler pulley axles 86 corresponding to the idler pulleys 82 of the embodiment of FIG. 3. The exemplary delivery handle of FIG. 3 further includes a tensioner assembly 90, the tensioner assembly 90 including a torsion spring 94, a tensioner arm 98, a tensioner pulley 102, a tensioner arm axle 106 and a tensioner pulley axle 112. In the presently described embodiment, the timing belt has teeth on one side (outer diameter or periphery) of the belt and the inner diameter (inner surface) is smooth or substantially smooth or flat. The smooth or flat surface of the timing belt 70 contacts the idler pulleys 82 and the tensioner pulley 102.

In the exemplary embodiment of FIG. 3, the outer support shaft 38 is fixed to the handle housing 14, and both the inner core 42 and outer sheath 34 are contained within the inner diameter of the outer shaft 38. The inner core 42 will be bonded at the proximal end along with a metal (e.g., stainless steel) shaft 30 to a female luer 116, which is coupled to or clamped into the handle body 14. In an aspect of the present invention, the metal shaft 30 may be bonded to the outer diameter of the inner core 42 to provide support/rigidity at the proximal end where the inner core 42 is unsupported in the handle body 10. The support of the metal shaft 30 over the inner core 42 mitigates potential deformation/buckling of proximal unsupported inner core 42 during stent deployment. As the outer sheath 34 is pulled back to release/deploy the stent, the inner core 42 is put into compression, therefore the unsupported proximal end of the inner core could deform. The bonded metal shaft 30 provides support and column strength to unsupported proximal inner core 42. The metal shaft 30 may be sized such that is slides over the outer diameter of the inner core 42 and through the inner diameter of the outer sheath 34. The metal shaft 30 does not impact the inner diameter of the inner core 42, so a guidewire (not shown) can still pass through entire assembly. A material other than metal may be used to for the support shaft, and the invention described herein is not limited to metal for use in the support shaft 30.

The outer sheath 34 is coupled to or bonded to the timing belt link 74 to deliver the stent by retracting the outer sheath 34 by movement of the thumbwheel, which in turn engages the teeth of the timing belt 70 via the inner barrel 66 and the teeth on the inner barrel 66. The metal shaft 30 that is coupled to or bonded to the inner core 42/female luer 116 is a guide rail that the outer sheath 34 and timing belt link 74 move proximally over during deployment.

Figure 4:
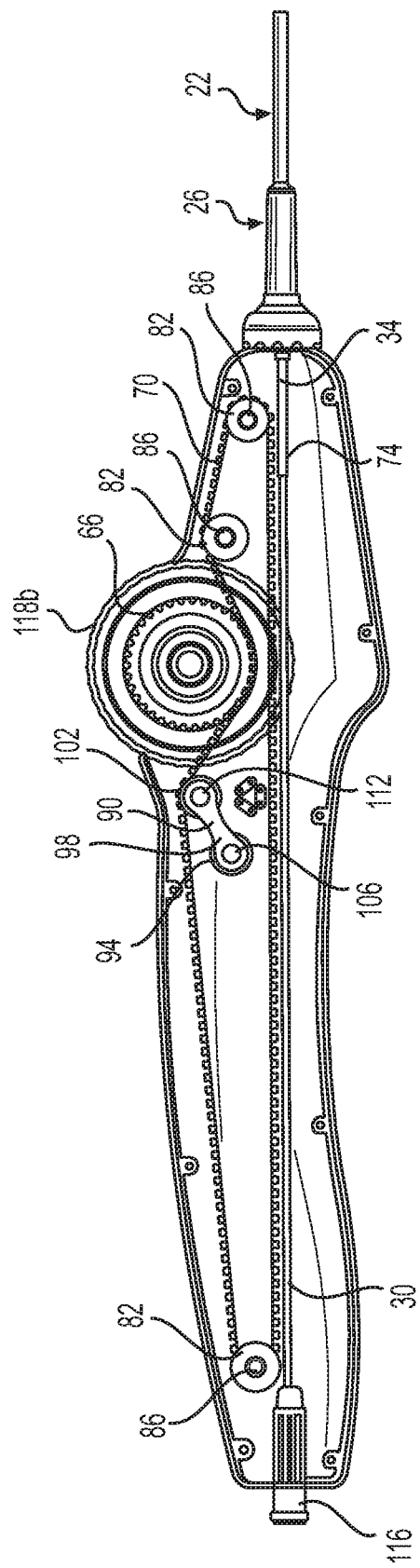
FIG. 4 is cross-sectional view of an assembled handle according to principles described herein

FIG. 4 is a cross-sectional view of an assembled handle according to principles described herein. The exemplary embodiment illustrated in FIG. 4 shows one part 114b of the two-part housing, where the respective two parts may be snap fit together for assembly. Other assembly methods may be used to mate the two parts together such as welding, bonding, gluing or other method. It is contemplated that each side of the two part housing is symmetrical and complementary, but such configuration is not required. The parts of the thumbwheel assembly 18 may be formed by molding, such as injection molding. The housing 14 may be unitary.

FIG. 4 illustrates one wheel of the thumbwheel assembly 18 that may comprise two wheels 118a and 118b, an axle 58, and a bearing 62. The bearing may include a ball bearing with an inner and outer grooved bearing race. The bearing serves to reduce rotational friction between the thumbwheel and the axle and may be eliminated if the frictional forces are acceptable. An acetal bushing or other method of friction reduction may be used in place of the bearing 62.

The wheels 118a and 118b may include teeth on an inner barrel 66 thereof. Although only one inner barrel is shown in FIG. 4 on wheel 118b, wheel 118a may also include an inner barrel with teeth. The teeth on the inner barrel 66 are sized to correspond with a timing belt 70. The inner barrel may be formed by molding, such as injection molding, and the teeth may be formed as part of the molding or other method such that the teeth are integral to the inner barrel 66. In another aspect, the teeth may be separable from the inner barrel 66.

As shown, the timing belt link 74 connects the outer sheath 34 to the timing belt 70. The exemplary handle of FIG. 4 further includes at least one idler pulley 82 for tensioning and guiding the timing belt 74. Also shown in FIG. 4 idler pulley axles 86 corresponding to the idler pulleys 82 of the embodiment of FIG. 4. The exemplary delivery handle of FIG. 4 further includes a tensioner assembly 90, the tensioner assembly 90 including a torsion spring 94, a tensioner arm 98, a tensioner pulley 102, a tensioner arm axle 106 and a tensioner pulley axle 112. In the exemplary embodiment of FIG. 4, the outer support shaft 38 is fixed to the handle housing 14, and both the inner core 42 and outer sheath 34 are contained within the inner diameter of the outer shaft 38. The inner core 42 will be bonded at the proximal end along with a metal (e.g., stainless steel) shaft 30 to a female luer 116, which is coupled to or clamped into the handle body 14.

Figure 5:
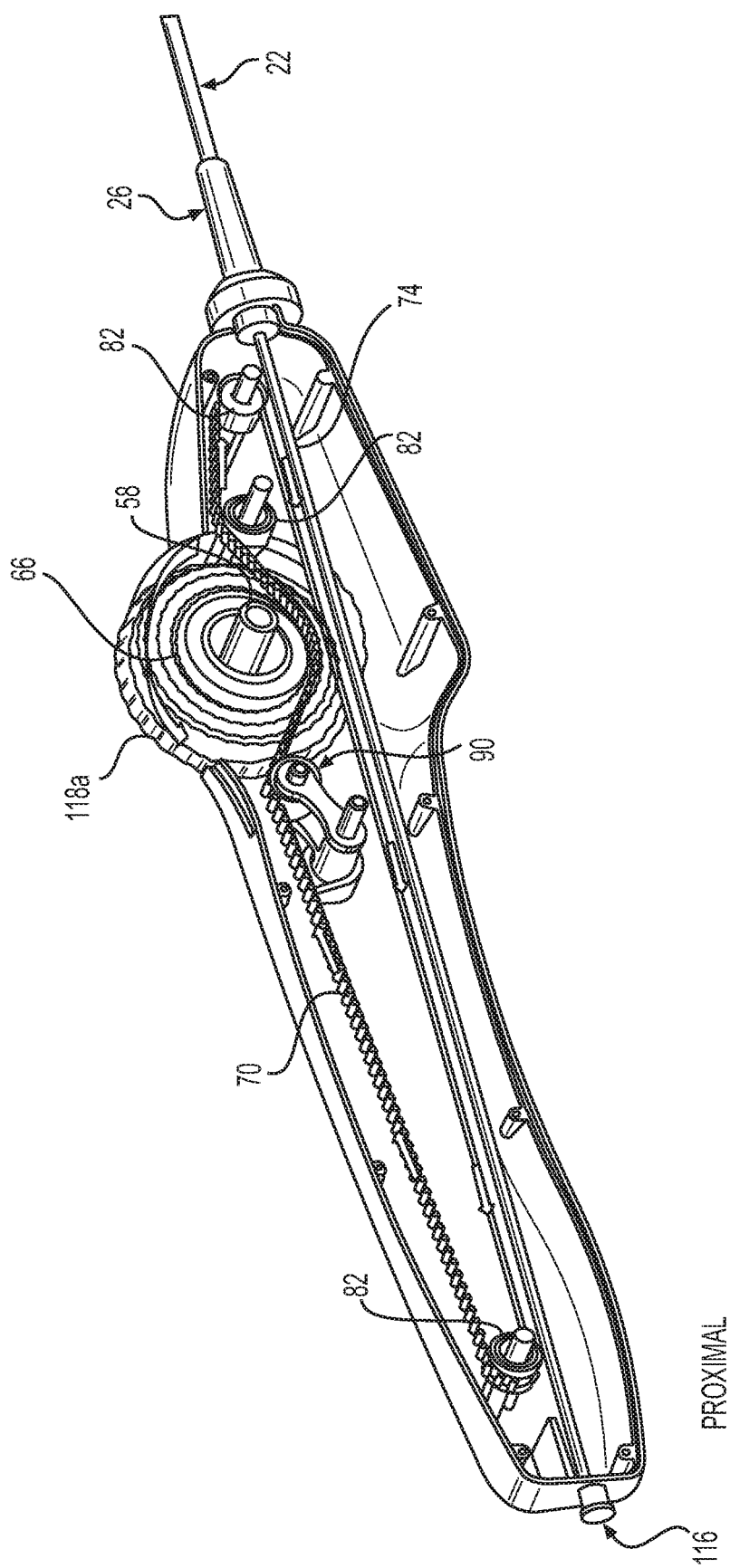
FIG. 5 is a cross-sectional view illustrating motion of the thumbwheel and the timing belt.

FIG. 5 further illustrates motion of the thumbwheel 18, timing belt 70 and timing belt link 74 for deployment of a stent according to principles described herein. As illustrated in FIG. 5, outer sheath 34 is translated proximally over guide tube/inner core 42 by the timing belt 70 by rotating the thumbwheel in the direction of the arrow. The timing belt 70 is driven by an operator via dual thumbwheel assembly 18, which may comprise integrally molded gear teeth, the pitch and shape of which correspond to teeth of the timing belt 70 for synchronizing/engaging the timing belt and causing movement of the timing belt to cause movement of the timing belt link, which is coupled to the outer sheath 34 to cause movement thereof for unsheathing (deploying) a stent provided therein. The diameter of the inner barrel 66, number of teeth on timing belt 70, and the pitch/frequency of the teeth on the timing belt 70 may each be adjusted/modified to allow for variable mechanical advantage during stent deployment and variable translation ratio. In addition, variable speed delivery may also be achieved by actuating the thumbwheel assembly 18 at the desired speed.

In the embodiment illustrated in FIG. 5, rotation of the portion thumbwheel 18 external to the handle proximally (in the direction of the arrow) causes an upper portion of the portion of the timing belt adjacent the portion of the thumbwheel internal to the handle to move distally (in the direction of the arrow). The timing belt 70 extends around an idler pulley 82 such that a portion of the timing belt 70 adjacent the timing belt link 74 move proximally (in the direction of the arrow), engaging the timing belt link 74 to move the timing belt link 74 proximally, which moves the outer sheath 34 coupled thereto proximally, thereby unsheathing the stent for deployment. Movement may be reversed for re-sheathing of catheter following stent deployment.

FIGS. 6(a)-(c) are cross-sectional views of the delivery device according to principles described herein and illustrates motion of the timing belt link 74 and outer sheath 34 upon movement of the thumbwheel 18 counterclockwise in the context of FIGS. 6(a)-(c). It should be appreciated that the direction of thumbwheel rotation described herein is described in the context of the cross-section provide, but that it is contemplated that the portion of thumbwheel external to the handle 14 will be rotated rearward (in a proximal direction). It is also contemplated that the configuration of the timing belt 70 may be adjusted (for example, looped over the thumbwheel) to modify the direction of rotation of the thumbwheel corresponding to the proximal movement (retraction) of the outer sheath 34.

As shown in FIG. 6(*a*), in an introducing position, the timing belt link is at a distal end of the handle housing. As the thumbwheel 18 is actuated in a predetermined direction, e.g. in the context of the cross-section shown, counterclockwise, the timing belt link/shuttle 74 moves proximally. Because the timing belt link/shuttle 74 is coupled to the outer sheath 34, the outer sheath moves proximally with the timing belt link/shuttle to expose a stent or other medical device mounted on the inner core 42 (not shown). FIG. 6(*b*) illustrates the positioning of the timing belt link/shuttle in a partially deployed position (e.g. the stent is partially deployed (not shown)). As the thumbwheel 18 is further rotated in a timing belt link/shuttle 74 further translates proximally to allow for full deployment of the stent or medical devices from the of the inner core 42, as shown in FIG. 6(*c*). In the embodiment here described, the thumbwheel 18 is actuated such that the upper side (external portion) of the thumbwheel is rotated proximally to cause the timing belt link/shuttle 74 to transit proximally. It is appreciated that the configuration/path of the timing belt 70 may be configured such that a distal rotation of the upper side (external portion) of the thumbwheel 18 may cause the timing belt link/shuttle 74 to transit proximally to cause the outer sheath 34 to retract from the inner core 42 to allow deployment of the medical device (not shown).

Figure 7:
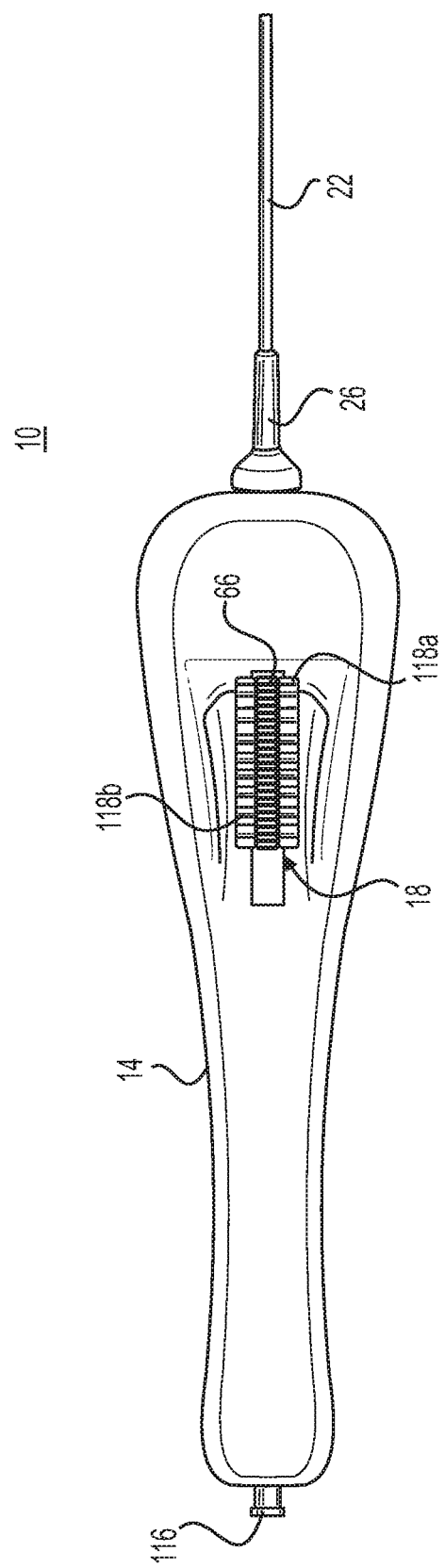
FIG. 7 is a top view of the delivery device according to principles described herein.

Although not shown in the figures, the thumbwheel may be a single thumbwheel with appropriate teeth corresponding to the teeth of the timing belt. As illustrated in the top view of FIG. 7, a thumbwheel comprising two wheels allows for a balanced design in which the catheter may exit the handle at a central portion of the distal end of the handle. FIG. 7 shows an assembled handle 10 and housing 14, and a thumbwheel assembly 18 having a first thumbwheel 118*a* and a second thumbwheel 118*b* separated by inner barrel 66. This configuration facilitates operation of the delivery device by holding the handle from either the left or the right side, allowing for comparable operation regardless of whether the operator is left or right handed.

Figure 8:
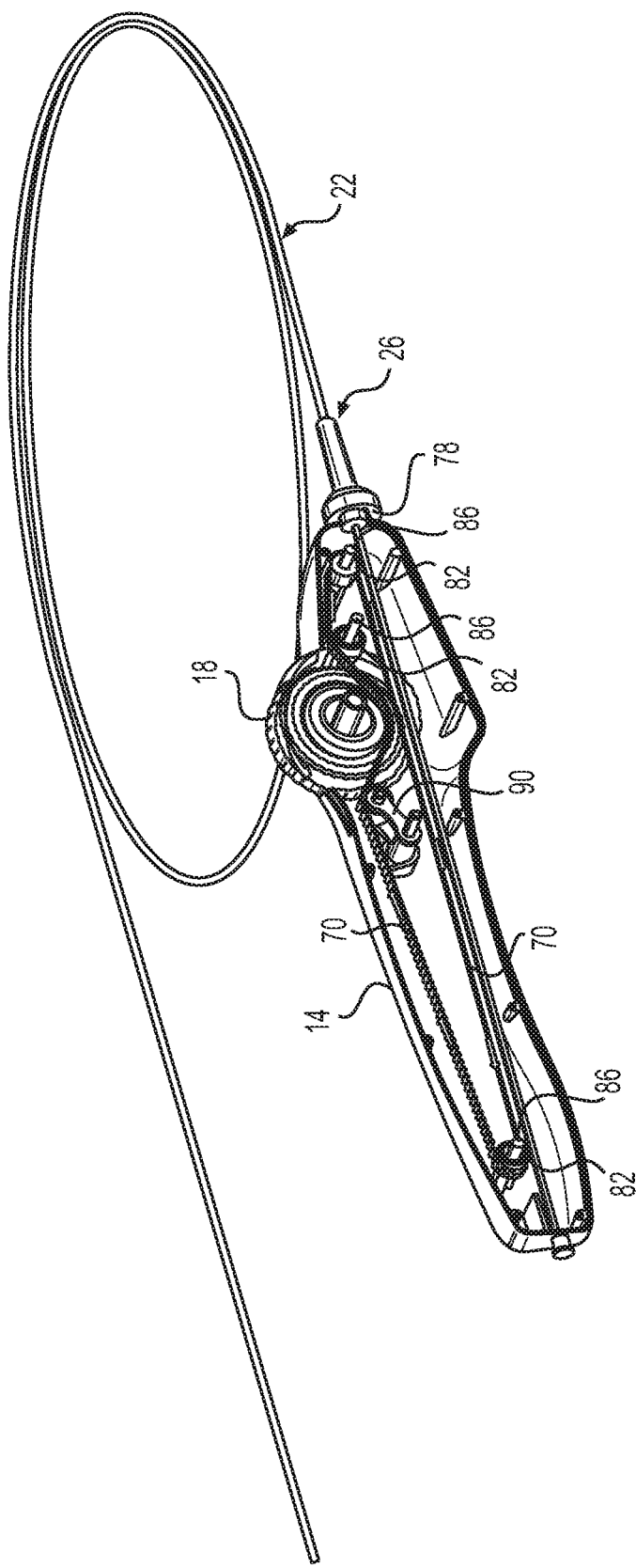
FIG. 8 illustrates a perspective view of the delivery device according to principles described herein, including the catheter device.

FIG. 8 illustrates a perspective view of the delivery device according to principles described herein, including the catheter device. As shown in FIG. 8, the timing belt 70 extends around idler pulleys 82 and the tensioner pulley 102 of tensioner 90. The tensioner pulley 102 is coupled to the torsion spring 94 via the tensioner arm 98. Tension is maintained on the timing belt by torsion spring 94 on tensioner arm axle 106, which urges the tensioner pulley 102 into contact with the timing belt 70 via the tensioner arm 98.

FIG. 9 is a cross-sectional line drawing showing detail of an exemplary embodiment of the thumbwheel assembly 18 and the timing belt link 74. As illustrated in FIG. 9, one part 118*b* of a two-part thumbwheel 18 has an outer surface 122 that may be textured for ease of use. The thumbwheel part 118*b* may also include an inner surface or rim 126. An inner barrel 66 extends from the thumbwheel part 118*b* and has a plurality of barrel teeth 130 thereon. The barrel teeth 130 on the inner barrel 66 are sized to correspond with a timing belt (not shown). Although not illustrated, the barrel teeth 130 may have a standard periodicity (pitch) or may have a variable periodicity (pitch) such that actuation of the thumbwheel assembly may cause movement of the timing belt (not shown) and thus translation of outer sheath 34 at a first rate when barrel teeth of a first periodicity engage the timing belt (not shown)_ and at a second rate when barrel teeth of a second periodicity engage the timing belt (not shown). Such variable rate may be imparted by having different spacing/periodicity/pitch of the teeth on the timing belt instead of or in addition to having different spacing/periodicity/pitch of the barrel teeth 130 on the inner barrel 66. FIG. 9 further illustrates the thumbwheel bearing 62 and the thumbwheel axle 58.

A safety locking feature (not shown) may be incorporated in the handle design such to mitigate inadvertent actuation of the handle during transit and storage. The safety locking feature may be a removal/disposal or toggle feature that engages the teeth on the inner barrel to lock it in place and prevent rotation. The safety locking feature may also be a feature that engages the timing belt link to prevent its translation.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments but should be defined only in accordance with the following claims and their equivalents.

What is claimed is:

1. A delivery device comprising:
   a catheter having three concentric shafts including an inner core, an outer sheath over the inner core and an outer support shaft;
   a flexible timing belt having a plurality of belt teeth on a surface of the flexible timing belt;
   a timing belt link coupled to the flexible timing belt and coupled to the outer sheath such that movement of the timing belt link causes movement of the outer sheath;
   a barrel having barrel teeth corresponding to belt teeth for directly engaging the belt teeth;
   a thumbwheel assembly having two thumbwheels, wherein at least a portion of at least one of the thumbwheels is integral with the barrel such that rotation of the thumbwheel assembly causes movement of the barrel such that the barrel teeth directly engage the belt teeth to cause movement of the flexible timing belt and the timing belt link, causing movement of the outer sheath, wherein the barrel and the two thumbwheels are rotatable about a common axis; and
   a belt tensioner comprising a torsion spring, a tensioner arm, and a tensioner pulley, the belt tensioner contacting a portion of the timing belt.

2. The delivery device of claim 1, further comprising a housing, wherein a portion of the thumbwheel is external to the housing, wherein the barrel is internal to the housing and the flexible timing belt is internal to the housing.

3. The delivery device of claim 1, wherein the belt teeth are on an outer surface of the flexible timing belt.

4. The delivery device of claim 1, further comprising at least one pulley, the flexible timing belt extending around the pulley such that the direction of rotation of the thumbwheel imparts a desired direction of translation of the outer sheath.

5. The delivery device of claim 1, wherein the belt tensioner further comprises a tensioner arm axle and a tensioner pulley axle.

6. The delivery device of claim 1, wherein the three concentric shafts comprise:
the inner core sized to receive a medical device thereon;
the outer sheath sized to receive the medical device in an unexpanded state on the inner core therein and to hold the medical device, the outer sheath translatable coaxially over the inner core; and
the outer support shaft at least partially extending over the inner core and the outer sheath.

7. The delivery device of claim 1, wherein the inner core and the outer support shaft are fixed with respect to a proximal end of the delivery device.

8. The delivery device of claim 7, wherein the metal shaft is bonded to the outer diameter of the inner core.

9. The delivery device of claim 7, wherein the metal shaft comprises stainless steel.

10. The delivery device of claim 1, further comprising a metal shaft at an outer diameter of the inner core.

11. The delivery device of claim 1, PEEK wherein the thumbwheel assembly is rotatable in a forward direction and a reverse direction such that the outer sheath translates in first direction when the thumbwheel assembly is rotated in the forward direction and the outer sheath translates in a second direction when the thumbwheel assembly is rotated in the reverse direction.

12. A system for delivery of an intraluminal stent, comprising:
a delivery device comprising:
a catheter having three concentric shafts including:
an inner core having the intraluminal stent thereon;
an outer sheath over the intraluminal stent in an unexpanded state on the inner core therein, the outer sheath holding the intraluminal stent in an unexpanded state, the outer sheath translatable coaxially over the inner core and the intraluminal stent; and
an outer support shaft at least partially extending over the inner core and the outer sheath;
a flexible timing belt having a plurality of belt teeth on a surface of the flexible timing belt;
a timing belt link coupled to the outer sheath such that movement of the timing belt link causes movement of the outer sheath to expose the intraluminal stent;
a barrel having barrel teeth corresponding to belt teeth;
a thumbwheel assembly having two thumbwheels, wherein at least a portion of at least one of the thumbwheels is integral with the barrel such that rotation of the thumbwheel assembly causes movement of the barrel such that the barrel teeth directly engage the belt teeth to cause movement of the flexible timing belt and the timing belt link, causing movement of the outer sheath; and
a belt tensioner comprising a torsion spring, a tensioner arm, and a tensioner pulley, the belt tensioner contacting a portion of the timing belt.

13. The delivery device of claim 12, further comprising a housing, wherein a portion of the thumbwheel is external to the housing, wherein the barrel is internal to the housing and the flexible timing belt is internal to the housing.

14. The delivery device of claim 12, wherein the belt teeth are on an outer surface of the flexible timing belt.

15. The delivery device of claim 12, further comprising at least one pulley, the flexible timing belt extending around the pulley such that the direction of rotation of the thumbwheel assembly imparts a desired direction of translation of the outer sheath.

16. The delivery device of claim 12, wherein the belt tensioner further comprises a tensioner arm axle and a tensioner pulley axle.

17. The delivery device of claim 12, further comprising a metal shaft at an outer diameter of the inner core.

18. The delivery device of claim 17, wherein the metal shaft is bonded to the outer diameter of the inner core.

19. The delivery device of claim 17, wherein the metal shaft comprises stainless steel.

20. The delivery device of claim 17, wherein the thumbwheel assembly is rotatable in a forward direction and a reverse direction such that the outer sheath translates in first direction when the thumbwheel assembly is rotated in the forward direction and the outer sheath translates in a second direction when the thumbwheel assembly is rotated in the reverse direction.

21. The delivery device of claim 12, wherein the outer support shaft and the inner core are fixed with respect to a proximal end of the delivery device.

22. A method of delivering a medical device to a body using a delivery device comprising a catheter having three concentric shafts including an inner core, an outer sheath over the inner core and an outer support shaft; a flexible timing belt having a plurality of belt teeth on a surface of the flexible timing belt; a belt tensioner comprising a torsion spring, a tensioner arm, and a tensioner pulley, the belt tensioner contacting a surface of the flexible timing belt a barrel having barrel teeth corresponding to belt teeth; a timing belt link coupled to the flexible timing belt and coupled to the outer sheath such that movement of the timing belt link causes movement of the outer sheath, a thumbwheel assembly comprising two thumbwheels coupled to and integral with the barrel such that rotation of the thumbwheel assembly causes movement of the barrel such that the barrel teeth directly engage the belt teeth to cause movement of the flexible timing belt and the timing belt link, causing movement of the outer sheath; wherein the barrel and the two thumbwheels are rotatable about a common axis; and a medical device over an outer diameter of the inner core; the method comprising:
rotating the thumbwheel assembly in a predetermined direction to cause the flexible timing belt to move in a direction associated with the predetermined direction of thumbwheel assembly rotation to cause the timing belt link to move the outer sheath in a desired direction; and
deploying the medical device from a distal end of the inner core to the body as the outer sheath moves in the desired direction.

23. The method of claim 22, wherein the three concentric shafts comprise:
the inner core, the inner core sized to receive a medical device thereon;
the outer sheath sized to receive the medical device in an unexpanded state on the inner core therein and to hold the medical device, the outer sheath translatable coaxially over the inner core; and
the outer support shaft at least partially extending over the inner core and the outer sheath.

24. The method of claim 22, wherein the inner core and the outer support shaft are fixed with respect to a proximal end of the delivery device.

25. The method of claim 22, further comprising a metal shaft at an outer diameter of the inner core.

26. The method of claim 25, wherein the metal shaft is bonded to the outer diameter of the inner core.

27. The method of claim 25, wherein the metal shaft comprises stainless steel.

28. The method of claim 25, wherein the thumbwheel assembly is rotatable in a forward direction and a reverse direction such that the outer sheath translates in first direction when the thumbwheel assembly is rotated in the forward direction and the outer sheath translates in a second direction when the thumbwheel assembly is rotated in the reverse direction.

\* \* \* \* \*

UNITED STATES PATENT AND TRADEMARK OFFICE
CERTIFICATE OF CORRECTION

Page 1 of 1

PATENT NO. : 10,987,239 B2
APPLICATION NO. : 16/599444
DATED : April 27, 2021
INVENTOR(S) : Michael A. Longo et al.

It is certified that error appears in the above-identified patent and that said Letters Patent is hereby corrected as shown below:

Claim 11 – Column 9, Line 25 – should read "...The delivery device of claim 1, wherein the..."

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*